(12) United States Patent
Ryan et al.

(10) Patent No.: US 7,621,880 B2
(45) Date of Patent: Nov. 24, 2009

(54) DOUBLE ENDED WIRE GUIDE

(75) Inventors: Walter N. Ryan, Bloomington, IN (US); Frank J. Fischer, Jr., Bloomington, IN (US); Thomas L. Foster, Poland, IN (US); Gary L. Butler, Bloomington, IN (US)

(73) Assignee: Vance Products Incorporated, Spencer, IN (US)

( * ) Notice: Subject to any disclaimer, the term of this patent is extended or adjusted under 35 U.S.C. 154(b) by 249 days.

(21) Appl. No.: 10/934,927

(22) Filed: Sep. 3, 2004

(65) Prior Publication Data

US 2005/0054953 A1    Mar. 10, 2005

Related U.S. Application Data

(60) Provisional application No. 60/500,447, filed on Sep. 5, 2003.

(51) Int. Cl.
*A61B 5/00* (2006.01)
*A61M 25/00* (2006.01)
*A61M 5/178* (2006.01)

(52) U.S. Cl. .............. 600/585; 604/171; 604/172; 604/523; 604/164.13

(58) Field of Classification Search .............. 600/585; 604/171, 172, 523, 164.13
See application file for complete search history.

(56) References Cited

U.S. PATENT DOCUMENTS

| | | | |
|---|---|---|---|
| 2,319,556 A | 5/1943 | Rhein et al. | |
| 3,301,393 A | 1/1967 | Regan, Jr. et al. | |
| 3,547,103 A | 12/1970 | Cook | |
| 4,003,369 A | 1/1977 | Heilman et al. | |
| 4,061,134 A | 12/1977 | Samuels et al. | |
| 4,548,206 A | 10/1985 | Osborne | |
| 4,643,305 A | 2/1987 | De Roure Olivier | |
| 4,721,117 A | 1/1988 | Mar et al. | |
| 4,763,647 A | 8/1988 | Gambale | |
| 4,846,186 A | 7/1989 | Box et al. | |
| 4,846,193 A | 7/1989 | Tremulis et al. | |

(Continued)

FOREIGN PATENT DOCUMENTS

| | | |
|---|---|---|
| JP | 2-226618 | 4/1992 |
| WO | WO 00/10636 | 3/2000 |

OTHER PUBLICATIONS

International Search Report for PCT Application PCT/US2004/028681, Search Report dated Feb. 1, 2005.

*Primary Examiner*—Max Hindenburg
*Assistant Examiner*—Jeffrey G. Hoekstra
(74) *Attorney, Agent, or Firm*—Brinks Hofer Gilson & Lione

(57) ABSTRACT

Double ended wire guides are manufactured so that either end, or both ends sequentially, may be inserted into a patient. The ends are different, so that the inventory requirements of wire guides are minimized. For example, a wire guide may have a straight end and an angled end, either end suitable for use on the patient. The wire guides may also differ in other characteristics, such as the stiffness or the diameters of the distal and proximal portions. The wire guide may also be stored in a package, the package including a fitting so that wetting solution may be injected into the package to wet the wire guide and prepare it for use.

22 Claims, 5 Drawing Sheets

U.S. PATENT DOCUMENTS

| | | | |
|---|---|---|---|
| 4,848,344 A | 7/1989 | Sos et al. | |
| 4,867,173 A | 9/1989 | Leoni | |
| 4,921,483 A | 5/1990 | Wijay et al. | |
| 4,925,445 A | 5/1990 | Sakamoto et al. | |
| 4,991,602 A | 2/1991 | Amplatz et al. | |
| 5,084,022 A * | 1/1992 | Claude | 604/164.13 |
| 5,120,308 A | 6/1992 | Hess | |
| 5,125,416 A | 6/1992 | Phillips | |
| 5,129,890 A | 7/1992 | Bates et al. | |
| 5,209,735 A | 5/1993 | Lazarus | |
| 5,213,111 A | 5/1993 | Cook et al. | |
| 5,217,007 A | 6/1993 | Ciaglia | |
| 5,243,996 A | 9/1993 | Hall | |
| 5,251,640 A | 10/1993 | Osborne | |
| 5,320,602 A | 6/1994 | Karpiel | |
| 5,324,304 A | 6/1994 | Rasmussen | |
| 5,363,847 A | 11/1994 | Viera | |
| 5,380,292 A | 1/1995 | Wilson | |
| 5,385,152 A | 1/1995 | Abele et al. | |
| 5,421,349 A | 6/1995 | Rodriguez et al. | |
| 5,568,865 A | 10/1996 | Mase et al. | |
| 5,573,010 A | 11/1996 | Pflugbeil | |
| 5,681,344 A | 10/1997 | Kelly | |
| 5,725,534 A | 3/1998 | Rasmussen | |
| 5,769,222 A | 6/1998 | Banerian | |
| 5,769,830 A | 6/1998 | Parker | |
| 5,772,609 A * | 6/1998 | Nguyen et al. | 600/585 |
| 5,776,079 A | 7/1998 | Cope et al. | |
| 5,797,857 A * | 8/1998 | Obitsu | 600/585 |
| 5,924,998 A | 7/1999 | Cornelius et al. | |
| 6,053,905 A | 4/2000 | Daignault, Jr. et al. | |
| 6,139,540 A | 10/2000 | Rost et al. | |
| 6,254,550 B1 | 7/2001 | McNamara et al. | |
| 6,409,717 B1 | 6/2002 | Israelsson et al. | |
| 6,569,106 B1 | 5/2003 | Ullman | |
| 6,588,588 B2 | 7/2003 | Samuels | |
| 2002/0072689 A1 | 6/2002 | Klint | |
| 2003/0060731 A1 | 3/2003 | Fleischhacker | |

\* cited by examiner

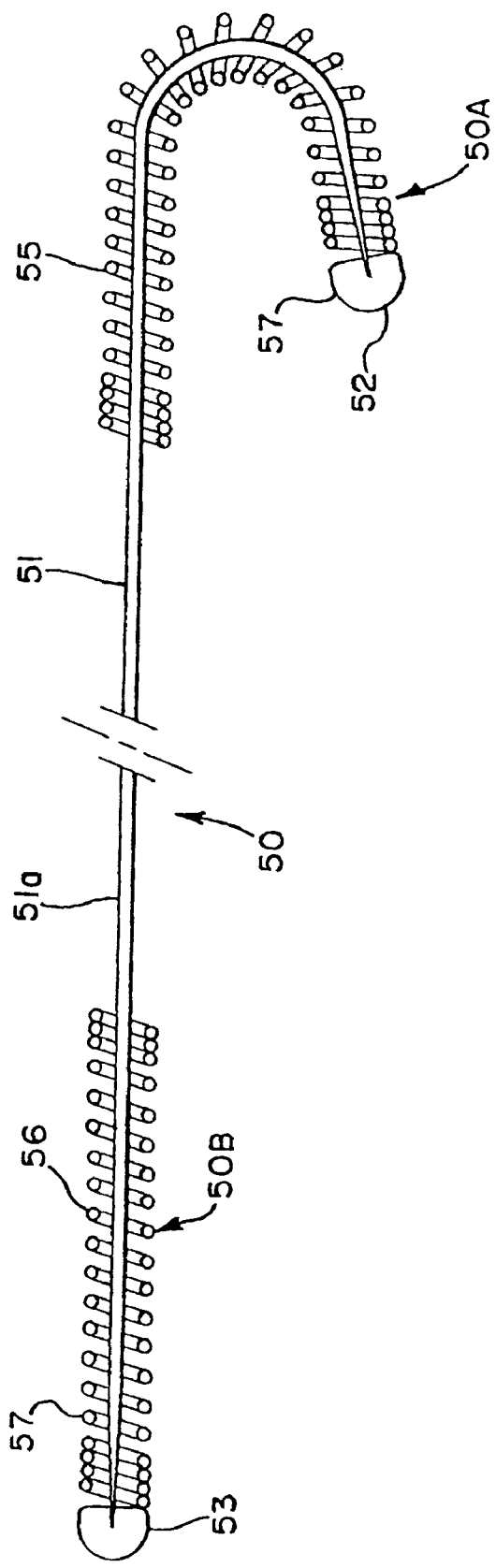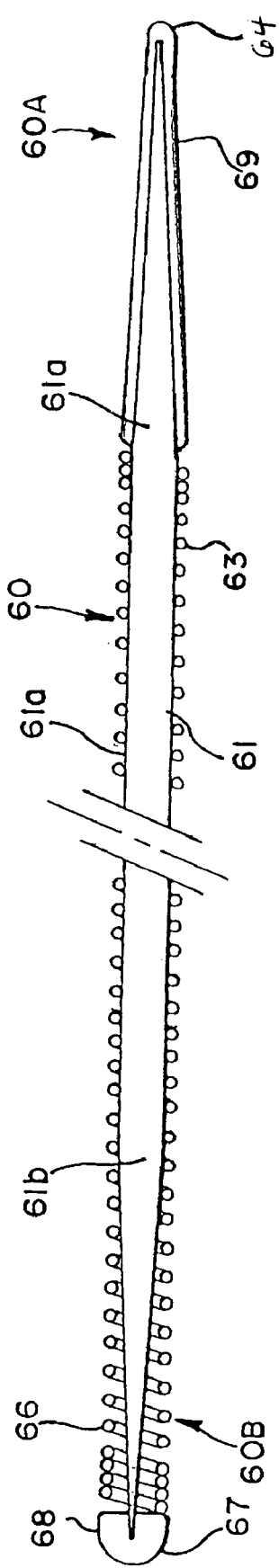

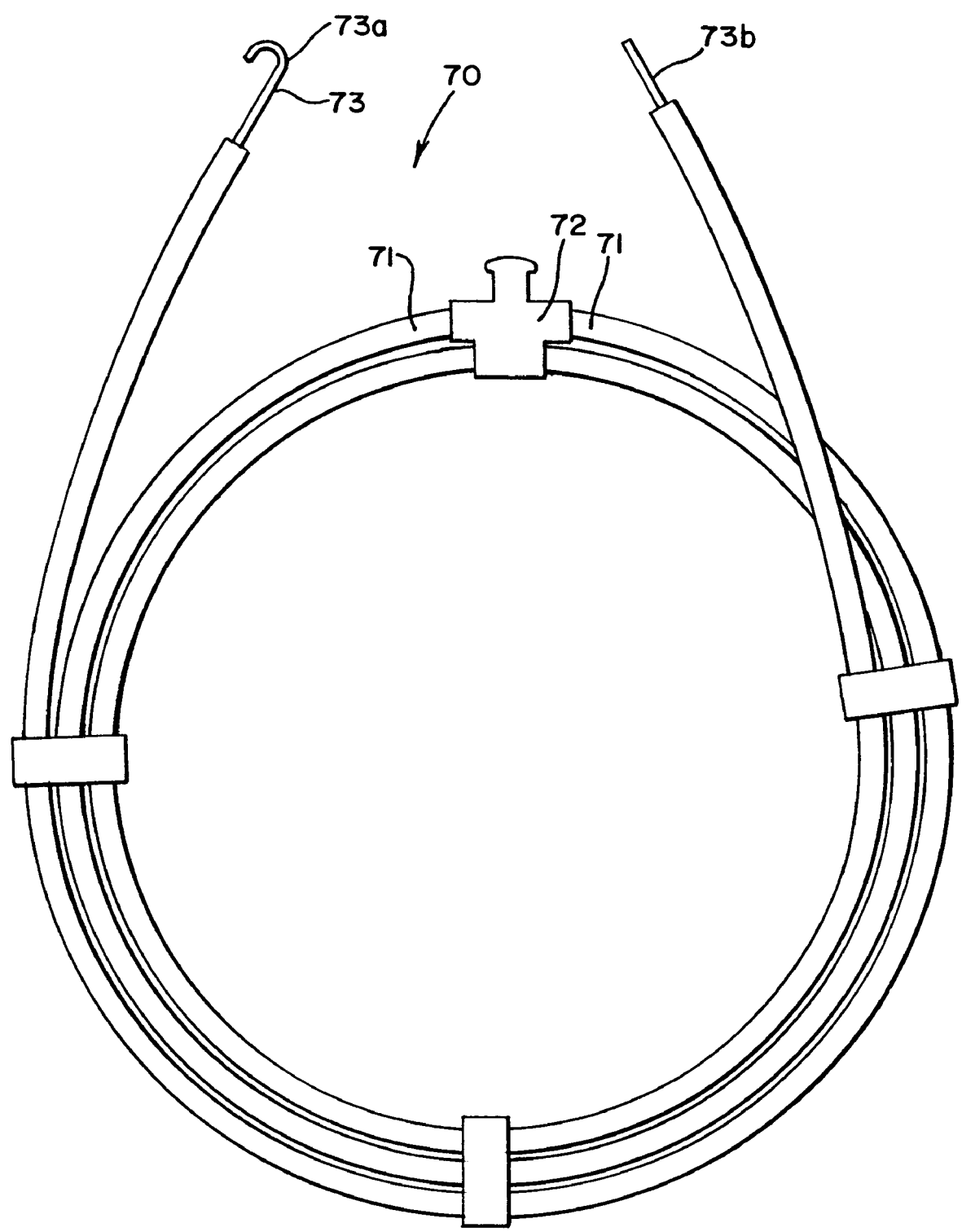

DOUBLE ENDED WIRE GUIDE

This application claims the benefit of the filing date under 35 U.S.C. § 119(e) of Provisional U.S. Patent Application Ser. No. 60/500,447, filed on Sep. 5, 2003, which is hereby incorporated by reference in its entirety.

TECHNICAL FIELD

The technical field is that of medical and surgical instruments and surgical procedures, and in particular wire guides, used to define a path within the body of a patient and allowing surgeons to use that path for access with diagnostic or therapeutic instruments.

BACKGROUND

Wire guides are used extensively in surgery to allow surgeons access to passageways and vessels within the body. These vessels may include vascular vessels, ureters, the urinary tract, the bile duct, the bowel and digestive tract, and others. Typically, surgeons wishing to introduce a catheter or other diagnostic or therapeutic instrument into such a passageway or vessel utilize the Seldinger technique which encompasses the exchange of instruments over a wire guide. One accepted method is to first introduce a wire guide into the patient, working the wire guide into the body of the patient in a minimally-invasive manner.

An example would be the use of a wire guide to introduce a catheter into a ureter. If a ureter is to be catheterized, a wire guide with a soft, non-traumatic tip is passed through the lumen of the ureter until it arrives at the kidney. The distal end of the wire guide is placed into a body orifice or opening and the surgeon works with the proximal end to infiltrate the wire guide through the ureter until it arrives at the kidney or other desired location. A catheter is then placed over the wire guide and the surgeon gently works the catheter down the wire guide until it arrives at the kidney or other desired location. When the catheter or other medical device is in place, the wire guide may be withdrawn.

Wire guides are used extensively and are available in a wide variety of sizes and shapes. Variables available include the diameter and length of the wire guide, the stiffness or flexibility of the shaft or body of the wire guide, the stiffness or flexibility of both the proximal and distal end, and whether or not the distal end has a curvature or an angle, ranging from a 5° angle, up to a 180° angle or even greater. Because of this great variety, and because wire guides are used in so many ways for so many surgical procedures, a hospital or surgical center may need to keep many wire guides in inventory to meet the needs of their patients and surgeons. In one example, wire guides may be available in seven diameters from 0.018 inches to 0.038, the body or shaft may be "stiff" or "flexible," and the tips may also be straight or manufactured at an angle from the longitudinal axis of the wire guide. In this example, then, a surgery center may need to inventory twenty-eight different wire guides, seven diameters in each of two shaft or body stiffnesses, and with an end that is either straight or angled.

Thus, because wire guides are so useful, it may be necessary to purchase and store a great many varieties in order to meet the needs of users. This requires hospitals and other users to purchase, store, and inventory a great many varieties of wire guides to meet all situations and needs. What is needed is a way to reduce the wire guide inventory requirements of hospitals and surgery centers. What is needed is a way to make wire guides more useful in a way that allows hospitals to reduce their inventory without sacrificing the variety of configurations available to patients and surgeons. The present invention is aimed at meeting these needs.

BRIEF SUMMARY

One aspect of the invention is an elongate wire guide comprising a distal end having a first angle for insertion into a patient, an intermediate portion, and a proximal end having a second angle, different from the first angle, for insertion into a patient, wherein the wire guide comprises an inner core and an outer plastic or elastomeric covering. Either end portion of the wire guide may be used for insertion into the patient, and the intermediate portion may be used to control the end portion that is inserted.

Another aspect of the invention is an elongate wire guide comprising a distal portion having a first stiffness with a distal end for insertion into a patient and a proximal portion having a second stiffness, different from the first stiffness, with a proximal end for insertion into a patient, wherein the wire guide comprises an inner core and an outer plastic or elastomeric covering. Either end portion of wire guides made according to these designs may also be inserted into the patient. The wire guide is controlled by the surgeon's use of proximal and distal portions.

Another aspect of the invention is an elongate wire guide comprising a distal portion having a first diameter and a distal end for insertion into a patient, and a proximal portion having a second diameter, different from the first diameter, and a proximal end for insertion into a patient, wherein the wire guide comprises an inner core and an outer plastic or elastomeric covering. Either end of wire guides made according to these designs may also be inserted into the patient, and are controlled by the surgeon's use of the proximal and distal portions.

Another aspect of the invention is a package for containing and wetting a double-ended wire guide, the package comprising a container and a fitting for connecting to a source of wetting solution, wherein the fitting is located about midway between ends of the container, and ends of the wire guide protrude from ends of the container. Another aspect of the invention is a package for containing and wetting a wire guide, the package comprising a container; and a fitting for connecting to a source of wetting solution, wherein the fitting is located about midway between ends of the container Another aspect of the invention is a method of making a double ended wire guide. The method comprises configuring a wire having a distal portion, an intermediate portion, and a proximal portion. The method also comprises enclosing the wire in a plastic or elastomeric covering, wherein the distal portion of the double ended wire guide has at least one property different from the proximal portion of the double ended wire guide, the at least one property selected from the group consisting of an angle of an end, a stiffness and a diameter.

Another aspect of the invention is a method of making a double ended wire guide. The method comprises configuring a wire having a distal portion, an intermediate portion, and a proximal portion. The method also comprises attaching a distal end and a proximal end to the wire and attaching first and second coil springs to the distal and proximal ends. The method also comprises coating the coil springs, the distal end and the proximal end, wherein the distal portion of the double ended wire guide has at least one property different from the proximal portion of the double ended wire guide, the at least one property selected from the group consisting of an angle of an end, a stiffness and a diameter.

BRIEF DESCRIPTION OF THE DRAWINGS

FIG. 5 is a partial cross section of a fifth embodiment of a double ended wire guide with an angled end and a straight end;

FIG. 6 is a partial cross section of another embodiment of a double ended wire guide with a stiffer portion and a more flexible portion, and two flexible, straight ends;

FIG. 7 is a perspective view of a container for a wire guide; and

DETAILED DESCRIPTION OF THE DRAWINGS AND THE PRESENTLY PREFERRED EMBODIMENTS

Figure 1:
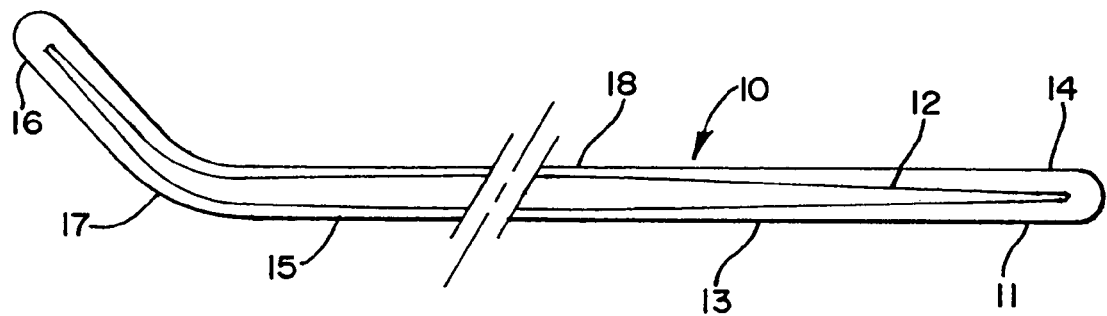
FIG. 1 is a partial cross section of a first embodiment of a double ended wire guide with a straight end and an angled end.

Wire guide embodiments have two ends that are suitable for use on the patient, a distal end and a proximal end of the wire guide. The end of the wire guide that is used inside the patient is manipulated or controlled by portions of the wire that are not inside the patient. FIG. 1 depicts a first embodiment of a double ended wire guide 10. In this embodiment, the wire guide is made from an outer covering 11 of a plastic material and an inner core wire 12 or mandril made from stainless steel or Nitinol. If mandril 12 is made from Nitinol or other shape-memory metal, it may be easily "trained" so that a 45° angle is its preferred shape at one end. The plastic material may be any medically acceptable material that is reasonably soft and atraumatic, such as polyurethane or silicone, and may include materials that are thermoplastic as well as thermoset. Other acceptable plastics may include polyethylene, PVC, polypropylene, and fluoropolymers such as PTFE. The wire guide has a distal portion 13 and a distal end 14. Wire guide 10 also has a proximal portion 15 and an angled proximal end 16, angled at about 45° to a longitudinal axis of the wire guide. The wire guide also includes an intermediate portion 18 between the distal and proximal portions. In this embodiment, distal end 14 is straight, aligned with a longitudinal axis of the wire guide. Proximal end 16, about the terminal 3 cm of the wire guide, is manufactured at about a 45° angle to the longitudinal axis of the wire guide. The angle may not always be apparent. If the wire guide is stored in a container, such as a straight container or a circular container, the angled end may be temporarily straightened out or the angle enhanced because of the way the wire guide is stored. Wire guides typically vary in overall length from about 60 to about 260 cm. Other lengths may be used.

In this example, inner wire or mandril 12 has the same decreasing diameter in both the distal and proximal portions, 13, 15. Both ends 14, 16 of the wire guide are flexible and suitable for insertion into the patient. The distal and proximal portions 13, 15, between ends 14, 16, may be considered an intermediate portion of guide wire 10. Distal end 14 in this embodiment is straight while proximal end 16 has an angle of 45° to the longitudinal axis of wire guide 10, though both tips will be rounded for ease of insertion into a body orifice of the patient. This configuration, of an angle at one end while the other end remains straight, may be achieved in several ways. The wire guide may also be coated with a hydrophilic coating 17, so that either end of the wire guide may be very lubricious after it is wetted with saline or other water solution.

One way to manufacture the embodiment of FIG. 1 is to use a solid core mandril or wire 12 made of Nitinol or other shape memory alloy. The wire is first manufactured to the desired size and is then "trained" to assume a configuration with one end straight and the other end at a desired angle. One way to do this is to form the wire, as with a form or a tool at a temperature below room temperature, and then to heat treat the shape memory alloy. Typically, temperatures in the range of 400-500° C. and times from 1-5 minutes are used. Other temperatures and times may also be used. Shape-memory or superelastic materials are heat treated or annealed from a weak (martinsite) structure to a strong (austenite) structure. The alloys are weak and deformable in the martinsitic state, which is thus useful for forming the wire. After transformation to the strong or martensitic state, the wire exhibits a superelastic property so long as the material remains above a transformation temperature, at which temperature it will revert to the martensitic state.

The transformation temperature is desirably a low temperature, well below the temperature of a human body, and preferably below room temperature, about 20-25° C. The transformation temperature of the wires is thus selected to be below the operating temperature of the wire, thus keeping the wire in a superelastic state. In this state, the wire advantageously returns to its original, unstressed shape when deforming stresses are removed, such as when the wire guide is removed from a package. The superelastic wire alloy also increasingly resists deformation as the stress load is increased. Thus, when a superelastic wire is deformed by being bent into a circular package for storage, the wire is placed into a state of stress. The straight end is stressed because it is bent into a circular shape with a radial dimension of the package used. The angled end is also placed into a state of stress because the angle may be partially straightened out or the angle may be exaggerated by being placed into the same package. When the wire is removed from the package, the stresses are removed, and the wire returns to its "normal" configuration of one straight end and one angled end.

The wires are formed by shaping the wires into the desired shape at room temperature or below, preferably with a cold mandril, and then annealing the properly-shaped wire at the proper annealing temperature for a time sufficient for the transformation to a superelastic state. In one example, a wire is formed from 0.010 inch diameter Ni—Ti Nitinol wire and is annealed at 800° F. (about 427° C.) for about 10 minutes. The time and temperature for annealing will vary with the alloy selected and with the diameter (thickness) of the wire. The wires themselves, not merely the annealing oven, must remain at the desired temperature for the proper length of time for the annealing or heat-treatment to be complete. Proper annealing is very important for the wires to return to the desired shape during use by the surgeon or physician using the wire guide.

The heat treat operation may also be used to determine the strength and modulus of the wire. In particular, the relative stiffness or flexibility of the wire may be determined by heat-treat methods that are well known in the art. The tensile or flexural modulus may be used as a measure of the relative stiffness or flexibility of the wire, although most physicians and operating room personnel can easily detect such differences with a quick "feel" or manipulation of the finished wire guide product. A stiff wire requires more force to bend or kink, while a more flexible wire requires less force to bend or kink. The stiffness or flexibility will be most apparent in the shaft or body of the wire guide, by which is meant the intermediate portion, the distal and proximal portions of the wire guide, less the very ends or tips of the wire guide, which will remain flexible and soft out of consideration for the patient.

The "trained" wire may then be coated with a plastic suitable for use in a wire guide. By "plastic" is meant any polymeric material suitable for medical use with the body of a patient. For instance, the wire may be placed into a mold and polyurethane injected, poured, or cast into the mold to cover and protect the wire. Alternatively, the wire may be dipped in a coating, or placed into a tool and injection molded with polyethylene, polypropylene, or polyvinyl chloride (PVC), or other materials. Other materials and manufacturing methods may be used to manufacture wire guides with a solid wire core and a plastic covering.

Figure 2:
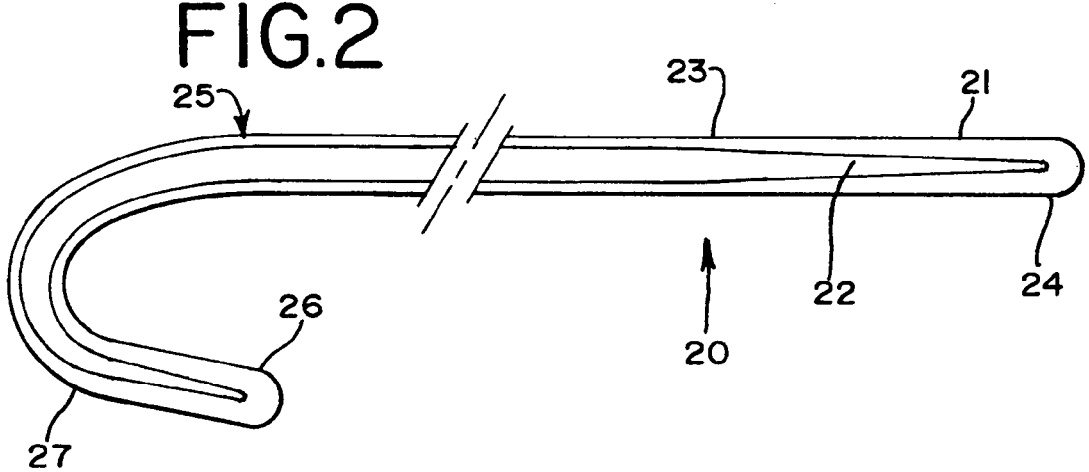
FIG. 2 is a partial cross section of a second embodiment of a double ended wire guide with a straight end and an end with a greater angle.

Another embodiment of a double-ended wire guide is depicted in FIG. 2. Wire guide 20 includes a softer plastic outer portion 21 and an inner mandril or solid wire core 22. Wire guide 20 has a distal portion 23 and a straight distal end 24, and a proximal portion 25 and a proximal end 26 that is angled at about 180°. The diameter of the wire guide 20 is the same in both the distal and proximal portions 23, 25, except for rounding at the two ends for easier insertion into a patient's body. In this embodiment, wire core 22 is preferably made from Nitinol or other shape memory metal. Wire core 22 has been formed so that it uniformly decreases from the center of wire guide 20 to the proximal and distal portions 23, 25. The wire may be formed by drawing, by grinding or by any other desired method. This wire guide will have two flexible ends 24, 26, with distal end 24 formed straight, and proximal end 26 angled with respect to the longitudinal axis of the wire guide. Outer portion 21, as described above for FIG. 1, may be made from any soft plastic material suitable for medical applications and may be added by injection molding or other plastic processing methods. Wire guide 20 may also be coated with a hydrophilic coating 27.

Figure 3:
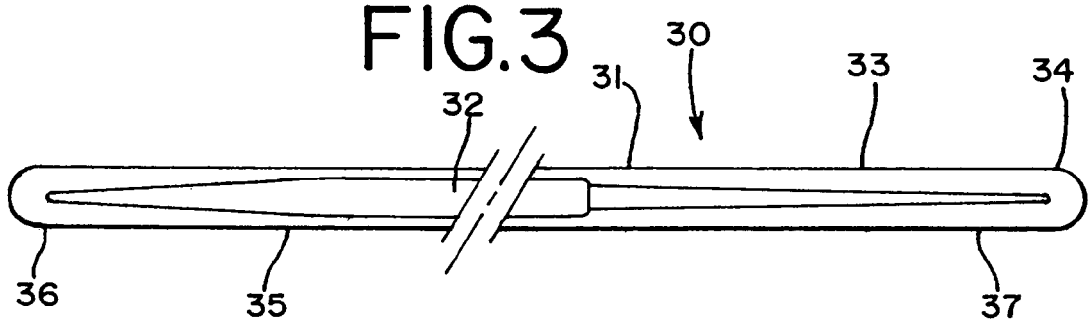
FIG. 3 is a partial cross section of a third embodiment of a double ended wire guide, having a mandril with a first diameter in one portion and a second diameter in another portion.

FIGS. 1 and 2 have provided embodiments in which a wire guide has both an angled end and a straight end. In another embodiment, a wire guide may have intermediate portions, the distal portion and the proximal portion, of two different stiffnesses. FIG. 3 depicts a wire guide 30 with an outer covering 31 and an inner wire core 32. Distal portion 33 and proximal portion 35 have the same outer, external diameter, but the inner wire core or mandril is different in distal portion 33 than in proximal portion 35. As discussed above for the embodiments of FIGS. 1 and 2, inner wire core may be a Nitinol wire, but it may also be a stainless steel or other suitable wire. Outer covering 31 may be a softer plastic material, such as polyurethane, polyethylene, polypropylene, or other suitable, medically acceptable plastic material. The outer plastic material may be added by any suitable step for molding or forming thermoplastic or thermoset materials, including insert molding, compression molding, casting, and so forth.

Flexible distal portion 33 has a flexural stiffness that is different from the flexural stiffness of proximal portion 35. A "stiff" portion requires more force to bend or kink than a "flexible" portion. The inner mandril 32 is depicted as having a greater diameter in proximal portion 35 than the diameter in distal portion 33. Therefore, distal portion 33, with the same outer diameter as proximal portion 35, will be composed of more plastic and less stainless steel or Nitinol. Proximal portion 35 will be stiffer because it is composed of less plastic and more stainless steel or Nitinol. Proximal portion 35 will therefore have a higher flexural modulus than distal portion 33. Both ends 34, 36 will be flexible, but the physician will enjoy differing degrees of control over the wire guide because of the differing stiffness in the portion that is inserted into the patient.

Figure 4:
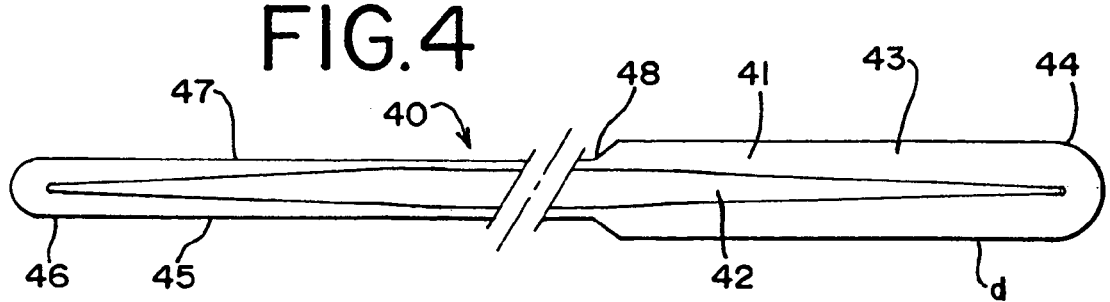
FIG. 4 is a partial cross section of a fourth embodiment of a double ended wire guide having a portion with a first diameter and another portion with a second diameter.

Another embodiment of a double ended wire guide is depicted in FIG. 4. Double ended wire guide 40 includes an outer covering 41 and an inner wire core 42. Wire guide 40 includes distal portion 43, distal end 44, proximal portion 45 and proximal end 46. The outer diameter d is greater in distal portion 43 than in proximal portion 45. Wire core 42 is desirably made from Nitinol or other shape-memory metal, or may also be made from stainless steel. Distal end 44 and proximal end 46 of the wire guide will be straight as shown, with no angle, and both ends will also be very flexible. Other variations of the double ended wire guides may also be used, e.g., any combination of an angle, a diameter, and a stiffness. Wire guide 40 may also be coated with a hydrophilic coating 47.

The transition from distal portion 43 to proximal portion 45 should be sufficiently gentle so as to be atraumatic to patients using wire guide 40. The transition 48 in FIG. 4 is greatly exaggerated for clarity. In reality, distal portion 43 may have a diameter of 0.025" while proximal portion 45 has a diameter of 0.018", so that transition 48 is only about 0.007 inches and is accomplished over about an inch of length of the wire guide. Alternatively, users may wish to have a transition that is more easily noticed, so the ends of the wire guide may be distinguished. In one example, a proximal portion may be made with a diameter of 0.038 inches while distal portion has a 0.018" diameter. Wire guide 40 may also be coated with a hydrophilic coating 47.

It may be desirable to distinguish the proximal portion from the distal portion in at least the wire guides in which there are diameter differences, as well as wire guides in which there is a flexibility difference. In these cases, the color of the outer covering may be used to distinguish. For instance, the proximal end may be molded in a first color and the distal end in a second color, the colors being formed from any suitable, non-toxic, colorants or from mixtures of the plastics themselves. For instance, if urethanes are used, the first color may be a natural tan or brown color, while a second color of black or white, or other color, may be achieved by adding a suitable colorant to one or more components of the urethane.

Other ways to distinguish the ends may also be used. For instance, small characters or a mark or marks may be molded onto the ends of the wire guide using the same tooling that is used for adding the plastic materials. Thus, the characters "035" or "025" may be molded onto ends having a diameter of 0.035" or 0.025" diameter. The characters that are molded should be rounded and smooth so as not to cause any trauma to the patient when the end marked with these characters is inserted into the patient. Other ways to distinguish the ends may also be used.

The embodiments thus far have focused on double ended wire guides made from an inner core wire and an outer plastic or polymeric covering. Other embodiments are also possible, such a coil-spring wire guide made with two ends that are different from each other. FIG. 5 depicts one such double ended wire guide 50. Wire guide 50 includes an inner mandril or safety wire 51 attached to a distal portion 50a, distal end 52, intermediate portion 51a, a proximal portion 50b, and a proximal end 53. Distal and proximal ends 52, 53 may be smooth metal hemispheres welded or soldered to safety wire 51. Ends 52, 53 may themselves be solder material. Proximal portion 50b includes a coiled wire 56 attached to proximal end 53, preferably by soldering, although other methods of attachment may be used. Distal portion 50*a* includes a coiled wire 55 attached to distal end 52, preferably by soldering, although other methods of attachment may be used. Coil wires 55, 56 may also be soldered or attached to wire 51 away from the distal and proximal ends.

Outer coil wires 55, 56 may be coated with a softer, plastic material 57 so as to be smoother and less traumatic to a patient. Ends 52, 53 may also be coated. Materials such as PTFE may be used. Wire guide 50 may also be coated with a hydrophilic coating. In this embodiment, inner wire or mandril 51 has been heat-treated or trained so that distal portion 50*a* of the wire guide has a 180° bend while proximal portion 50*a* is straight.

Another embodiment of a double ended wire guide is depicted in FIG. 6. Wire guide 60 has a distal portion 60*a*, an intermediate portion 61*a*, and a proximal portion 60*b*. Wire guide 60 includes an inner mandril 61 having a greater width or diameter 61*a* in intermediate portion 61*a* and a narrower width or diameter 61*a*, 61*b* in the proximal and distal portions. Coil spring 63 extends over proximal portion 60*b* and intermediate portion 61*a*. Wire guide 60, including coil spring 63 and ends 64, 67 may be covered with a smooth and non-traumatic coating 66, for example, PTFE. In addition, wire guide 60 may also be coated with a hydrophilic coating 68. In this embodiment, distal portion 60*a* will be more flexible because of the smaller diameter of distal portion 61*a* of the mandril. Proximal portion 60*b* will have a stiffness different from the stiffness of distal portion 60*a*. Of course, other embodiments besides those described are also possible. For example, some surgeons may prefer a wire guide with a very stiff central or intermediate portion, much stiffer than the distal or proximal ends of the wire guide. Thus, the wire guide depicted in FIG. 6 may be constructed with a very stiff intermediate portion, including a wider, less-flexible core wire and an outer coil spring that extends throughout the intermediate portion. The core wire, as discussed above, may be made from Nitinol or a stainless steel. In one example of a stiffer intermediate portion, the core wire for a 0.035 inch wire guide is 0.021 inches diameter Nitinol, with a coil spring assembled over the wire and then coated as desired with PTFE or urethane to a 0.035 inch diameter. The distal and proximal portions of the core wire may be tapered thinner, and coated with an outer jacket of urethane or PTFE, the distal and proximal portions straight or angled as described above. The proximal portion may be tapered to be even more flexible than the distal portion, with the core wire ground to the thickness of a hair, only a few thousandths of an inch in diameter (0.001 to 0.002 inches, about 0.025 to 0.051 mm). The core wire, and the transitions from a thicker intermediate portion to thinner distal and proximal portions, is preferably made via centerless grinding. The coil spring may coated with a PTFE coating, or a urethane coating. In some applications, the distal portion may be coated with a thinner, more flexible urethane coating 69, and the proximal portion with PTFE coating 66.

Once the surgeon has selected the configuration of the wire guide, it is desirable to wet the wire guide, in order to make the surface slick and lubricious, for ease of insertion into the patient. As noted above, wire guides are desirably coated with a smooth plastic for ease of insertion. Wire guides may also be coated with a hydrophilic coating so that when wetted with water or saline solution, the surface has a very low surface tension, is easily wetted, and is so much more lubricious.

Accordingly, double ended wire guides, or standard wire guides, may be packaged in a container as depicted in FIG. 7. Wire guide container 70 includes hollow plastic tubing segments 71 attached to either side of a fitting 72. Fitting 72 is thus located centrally within the container, with at least roughly equal lengths of tubing on either side of the fitting. Container 70 contains a wire guide 73, shown with ends 73*a*, 73*b* protruding from the tubing. Container 70 and wire guide 73 may be stored in a sterile plastic overwrap or package (not shown). Fitting 72 may be any convenient fitting, such as a Luer lock fitting, for admitting saline or other water solution for wetting wire guide 73. Wire guide 73 may be a double-ended wire guide as described above, or may be a single ended standard wire guide. Saline from a syringe or other source may be admitted to package 70 by injecting or otherwise admitting saline solution. Other water solutions may also be used to wet wire guide 73 and prepare it for use by the surgeon. The advantage of this tubing and the centrally-located fitting is that both ends of the wire guide are wetted quickly and easily from a single location, the centrally-located fitting.

Figure 8:
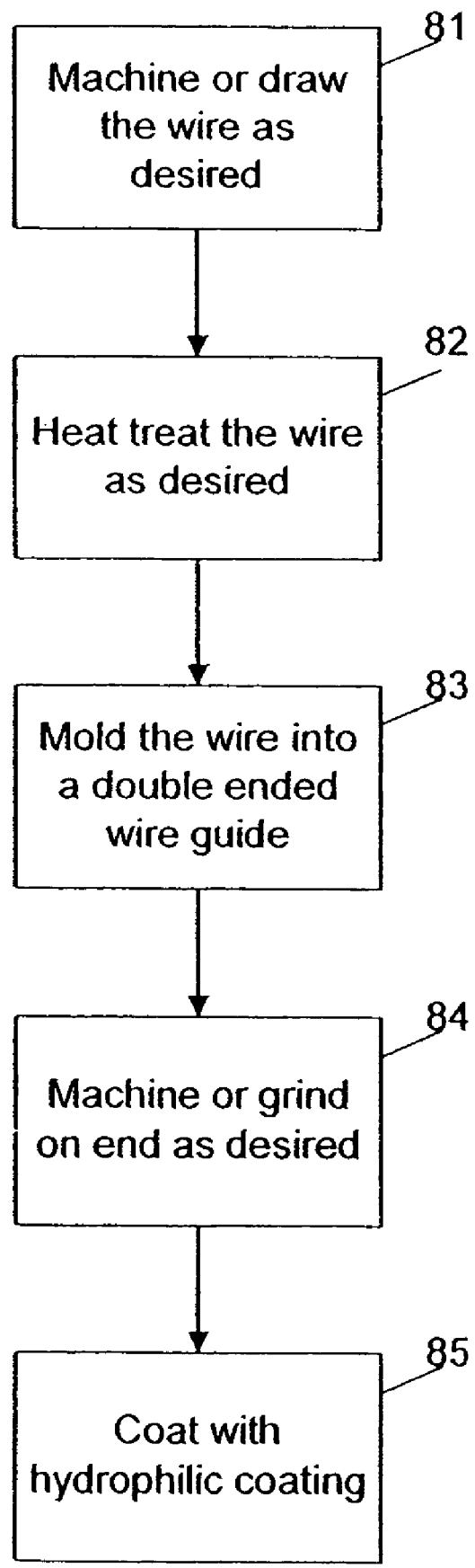
FIGS. 8 and 9 are flowcharts for methods of making a double-ended wire guide.
Figure 9:
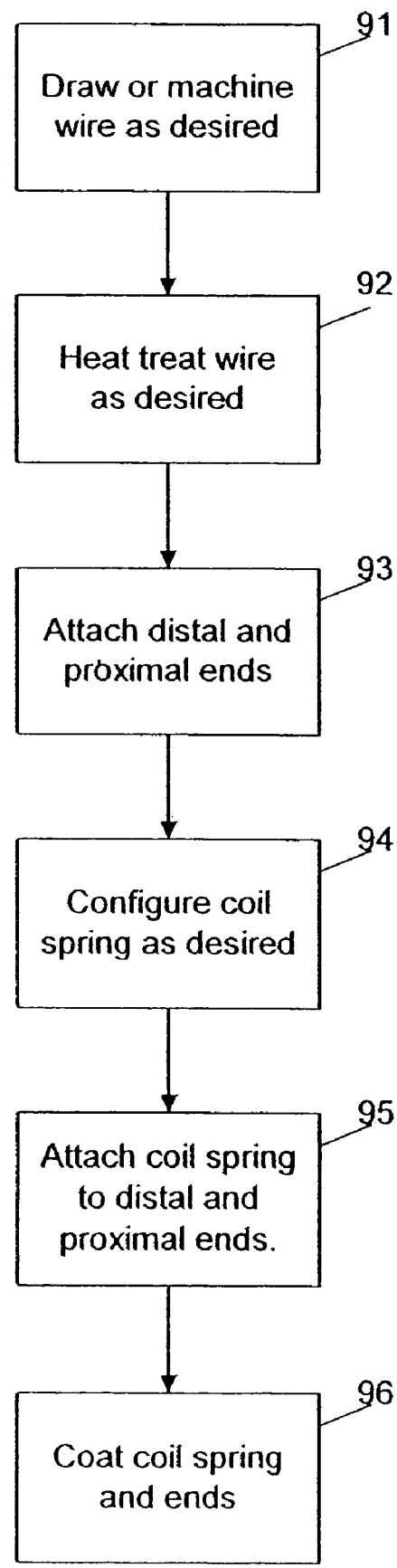

There are several ways to make double ended wire guides according to the present invention, as depicted in FIGS. 8 and 9. FIG. 8 is a flowchart depicting a method of manufacturing a double ended wire guide, of the type including a core wire and an outer plastic covering. A first step is to configure the core wire, such as by machining or drawing 81 the wire to the desired dimensions, such as length and the diameters of the distal and proximal portions of the wire. If the wire is Nitinol or other shape-memory alloy, the wire should be heat-treated 82 or trained as desired, such as by heat-treating a desired angle on one or both ends of the wire. The wire is then molded 83 into a double ended wire guide by a plastics-processing method. The molded wire guide may then be machined or ground 84 if desired. In some embodiments, the molded wire guide may be coated with another smooth plastic, such as PTFE or other fluorocarbon coating. The wire guide may then be desirably coated 85 with a hydrophilic coating.

Another way of making a double ended wire guide is depicted in FIG. 9. This process applies primarily to double ended wire guides using an internal wire or mandril and an outside coil spring, along with smooth distal and proximal ends. A first step in the method is to configure a core wire, such as a Nitinol wire or stainless steel wire, which may be drawn or machined 91 to the desired shapes or diameters. The wire may then be heat treated 92, for instance to shape desired angles, if the wire is made of Nitinol or other shape memory alloy. The distal and proximal ends are formed and attached 93. A coil spring is then purchased or configured 94 as desired, for instance by winding with a first larger diameter for one end and the central portion of the spring, and a smaller diameter for the other end of the spring. The coil spring is then attached 95 to the distal and proximal end portions. The coil spring and the ends may then be coated 96 with a smooth polymeric coating, such as PTFE, and may also be coated with a hydrophilic coating.

There are many ways to practice the invention. One of the useful features of embodiments of the invention is the ability to use either end of the wire guide. With embodiments of the present invention, the number of wire guides kept in an institution's inventory may be reduced. A single wire guide may thus have two useful ends, as described above, rather than only one. The two ends may share some common features, such as the same diameter, while differing in some performance aspect, such as the angles of the ends or the stiffnesses of the ends. It is also possible to combine features of wire guides in other ways since both ends may be used on the same patient. For instance, if it is known that certain procedures require the use of more than one wire guide, such as a sequence of increasing diameters or a sequence of increasing stiffnesses, appropriate combinations may be made on a single wire guide to minimize the number of wire guides used for a particular patient.

The invention has been described in terms of embodiments useful for wire guides made with an internal wire or mandril and an external plastic or polymer surface. Other embodiments may be include wire guides made with other techniques or combinations of materials, such as wire guides that are made from an internal safety wire and an external coil wire. Embodiments of the invention are not limited to these two types, nor to those depicted in the drawings. Other embodiments may be used in other applications and in many areas of the body. These embodiments are not limited to human bodies, but may be used in veterinary service as well. Other aspects of the invention, such as the packaging for wire guides, are also not limited to the embodiment shown and described, but is meant to apply to other embodiments.

Accordingly, it is the intention of the applicants to protect all variations and modifications within the valid scope of the present invention. It is intended that the invention be defined by the following claims, including all equivalents. Since the foregoing detailed description has described only a few of the many alternative forms this invention can take, it is intended that only the following claims, including all equivalents, be regarded as a definition of this invention.

What is claimed is:

1. An elongate wire guide comprising:
a distal portion having a distal end having a first angle for insertion into a patient; a proximal portion having a proximal end having a second angle, different from the first angle, for insertion into the patient, wherein the distal portion and the proximal portion are adapted to be independently inserted into the patient based on the angle that is particularly suited for a procedure or a portion of a procedure being performed;
an intermediate portion between the distal portion and the proximal portion;
wherein the wire guide comprises an inner superelastic core and an outer covering;
wherein a stiffness of the distal portion and a stiffness of the proximal portion are each less than a stiffness of the intermediate portion;
wherein the distal end and the proximal end each resist deformation and have an original, unstressed shape to which they return upon removal of a deforming stress;
wherein the inner core of at least one of the distal portion, the proximal portion, and the intermediate portion is heat treated to affect, alter, or change the stiffness of the respective one of the distal portion, the proximal portion, and the intermediate portion;
wherein the inner core distal portion has at least a first and a second diameter, the second diameter being closer to the distal end and less than the first diameter;
the inner core proximal portion has at least a first and second diameter, the second diameter being closer to the proximal end and less than the first diameter; and
wherein at least one of the distal portion or the proximal portion further comprises a coil spring.

2. The wire guide according to claim 1, wherein a diameter of the distal portion is different from a diameter of the proximal portion.

3. The wire guide according to claim 1, wherein the distal portion is more flexible and the proximal portion is stiffer.

4. The wire guide according to claim 1, wherein the stiffness of the distal and proximal portions is tailored by varying a thickness of the inner core or the outer covering.

5. The wire guide according to claim 1, wherein the stiffness of the distal portion or the stiffness of the proximal portion is tailored by adjusting an outer diameter of the distal portion or an outer diameter of the proximal portion or by adjusting a diameter of the inner core.

6. The wire guide according to claim 1, wherein at least one of the proximal and distal portions further comprise a hydrophilic coating.

7. The wire guide of claim 1, further comprising a mark or color identifying at least one of the distal and proximal portions.

8. The wire guide according to claim 1, wherein the outer covering is a plastic or elastomeric covering.

9. An elongate wire guide comprising:
a distal portion having a first stiffness and a distal end for insertion into a patient; a proximal portion having a second stiffness, different from the first stiffness, and a proximal end for insertion into the patient, wherein the distal portion and the proximal portion are adapted to be independently inserted into the patient based on the stiffness that is particularly suited for a procedure or portion of a procedure being performed;
an intermediate portion between the distal portion and the proximal portion;
wherein the wire guide comprises an inner superelastic core and an outer covering;
wherein a stiffness of the distal portion and a stiffness of the proximal portion are each less than a stiffness of the intermediate portion;
wherein the distal end and the proximal end each resist deformation and have an original, unstressed shape to which they return upon removal of a deforming stress;
wherein the inner core of at least one of the distal portion, the proximal portion, and the intermediate portion is heat treated to affect, alter, or change the stiffness of the respective one of the distal portion, the proximal portion, and the intermediate portion;
wherein the inner core distal portion has at least a first and a second diameter, the second diameter being closer to the distal end and less than the first diameter;
the inner core proximal portion has at least a first and second diameter, the second diameter being closer to the proximal end and less than the first diameter; and
wherein at least one of the distal portion or the proximal portion further comprises a coil spring.

10. The wire guide according to claim 9, wherein the distal end is angled, and the proximal end is straight, with respect to a longitudinal axis of the wire guide.

11. The wire guide according to claim 9 wherein the stiffness of the distal portion or the stiffness of the proximal portion is tailored by varying a thickness of the inner core or the outer covering.

12. The wire guide according to claim 9 wherein the stiffness of the distal portion or the stiffness of the proximal portion is tailored by adjusting an outer diameter of the distal portion or an outer diameter of the proximal portion or by adjusting a diameter of the inner core.

13. The wire guide according to claim 9, wherein at least one of the proximal and distal portions further comprise a hydrophilic coating.

14. The wire guide of claim 9, further comprising a mark or color identifying at least one of the distal and proximal portions.

15. The wire guide according to claim 9, wherein the outer covering is a plastic or elastomeric covering.

16. An elongate wire guide comprising:

a distal portion having a first diameter and a distal end for insertion into a patient; a proximal portion having a second diameter, different from the first diameter, and a proximal end for insertion into the patient, wherein the distal portion and the proximal portion are configured to be independently inserted into the patient based on the diameter that is particularly suited for a procedure or portion of a procedure being performed;

an intermediate portion between the distal portion and the proximal portion;

wherein the wire guide comprises an inner superelastic core and an outer covering;

wherein a stiffness of the distal portion and a stiffness of the proximal portion are each less than a stiffness of the intermediate portion;

wherein the distal end and the proximal end each resist deformation and have an original, unstressed shape to which they return upon removal of a deforming stress;

wherein the inner core of at least one of the distal portion, the proximal portion, and the intermediate portion is heat treated to affect, alter, or change the stiffness of the respective one of the distal portion, the proximal portion, and the intermediate portion;

wherein the inner core distal portion has at least a first and a second diameter, the second diameter being closer to the distal end and less than the first diameter;

the inner core proximal portion has at least a first and second diameter, the second diameter being closer to the proximal end and less than the first diameter; and wherein at least one of the distal portion or the proximal portion further comprises a coil spring.

17. The wire guide according to claim 16, wherein the distal portion is angled and the proximal portion is straight.

18. The wire guide according to claim 16, wherein the distal portion is less stiff than the proximal portion.

19. The wire guide of claim 16, further comprising a mark or color identifying at least one of the distal and proximal portions.

20. The wire guide according to claim 16, wherein at least one of the proximal and distal portions further comprise a hydrophilic coating.

21. The wire guide according to claim 16, wherein the outer covering is a plastic or elastomeric covering.

22. The wire guide according to claim 16 wherein the distal portion has at least one property different from the proximal portion, the at least one property selected from the group consisting of an angle of an end, a stiffness, and a diameter.

* * * * *